(12) United States Patent
Dieterle et al.

(10) Patent No.: US 8,084,262 B2
(45) Date of Patent: Dec. 27, 2011

(54) BIOMARKER FOR FARNESYL PATHWAY

(75) Inventors: Frank Dieterle, Basel (CH); Goetz Schlotterbeck, Efringen-Kirchen (DE); Hans Senn, Windisch (CH); Laura Suter-Dick, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 9 days.

(21) Appl. No.: 12/295,343

(22) PCT Filed: Mar. 28, 2007

(86) PCT No.: PCT/EP2007/002747
§ 371 (c)(1),
(2), (4) Date: Sep. 30, 2008

(87) PCT Pub. No.: WO2007/112906
PCT Pub. Date: Oct. 11, 2007

(65) Prior Publication Data
US 2009/0130770 A1    May 21, 2009

(30) Foreign Application Priority Data
Apr. 5, 2006 (EP) ..................... 06112264

(51) Int. Cl.
*G01N 33/00* (2006.01)

(52) U.S. Cl. .......... 436/89; 436/86; 436/106; 436/119
(58) Field of Classification Search .............. None
See application file for complete search history.

(56) References Cited

OTHER PUBLICATIONS

Hendriks et al. "Isolation and characterisation of renal metabolites of gamma-glutamylfeinylglycine in the urine of the domestic cat (*Felis catus*)". 2004. Comparative Biochemistry and Physiology, Part B. vol. 139. pp. 245-251.*
Daniels et al, "One-pot synthesis of L-felinine" Tetrahedron Letters 1999, 40, 4463-4465.*
Hendriks et al., "Felinine: A Urinary Amino Acid of Felidae", Comparative Biochemistry and Physiology, vol. 112B, No. 4, pp. 581-588 (1995).
Reszka et al., "Nitrogen-Containing Bisphosphonate Mechanism of Action", Mini Reviews in Medicinal Chemistry, vol. 4, No. 7, pp. 711-719 (2004).

* cited by examiner

*Primary Examiner* — Yelena G Gakh
*Assistant Examiner* — David Weisz
(74) *Attorney, Agent, or Firm* — George W. Johnston; Dennis P. Tramaloni

(57) ABSTRACT

The invention generally provides methods to determine the extent to which a compound interferes with steroid metabolism, comprising a novel biomarker of a felinine derivative. The invention also provides such novel felinine derivative biomarker.

5 Claims, 14 Drawing Sheets

Variante 1

Variante 2

BIOMARKER FOR FARNESYL PATHWAY

Figure 1A:
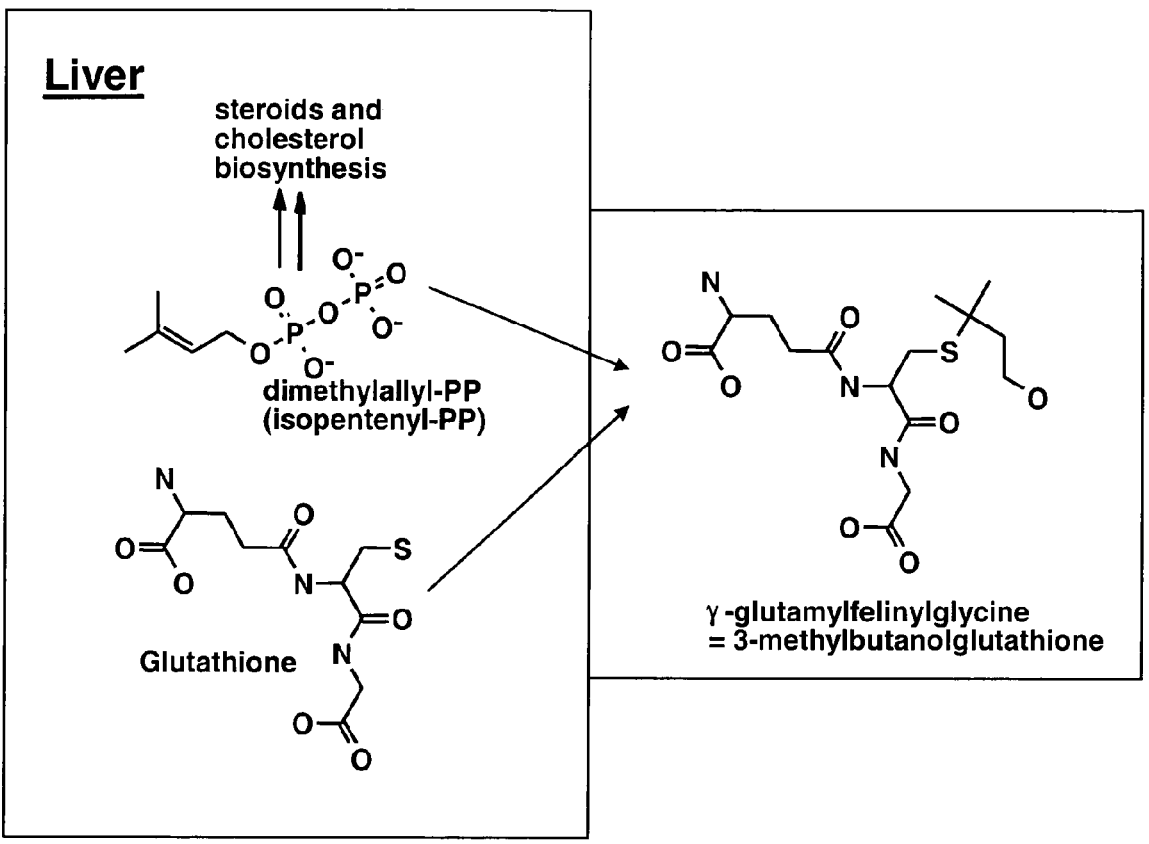

Bisphosphonates and especially Aminobisphosphonate inhibit a key enzyme within the mevalonate pathway, farnesyl diphosphate (FPP) synthase (Green J R. Bisphosphonates: preclinical review. The Oncologist 2004; 9(Suppl4):3-13). Inhibition of this enzyme leads to a reduction in protein prenylation (Rogers M J, Gordon S, Benford H L, Coxon F P, Luckman S P, Mönkkönen J, Frith J C. Cellular and molecular mechanisms of action of bisphosphonates. Cancer. 2000; 88(12 Suppl):2961-78). As a consequence, the production of FPP and, thus, the biosynthesis of squalene and sterol (cholesterol) is affected. But also the isoprenylation of signaling proteins which involves the transfer of a farnesyl or geranylgeranyl group onto a cysteine amino acid residue of the protein are hampered. Isoprenylation is a posttranslational modification necessary for full activation of several key proteins involved in a number of metabolic pathways which underlie cell survival, cytoskeletal organisation and cancer progression (Green J R. Bisphosphonates: preclinical review. The Oncologist 2004; 9(Suppl4):3-13; Wakeling A E. Inhibitors of growth factor signalling. Endocr Relat Cancer. 2005 July; 12 Suppl 1:S183-7). The pathways in which bisphosphonates interfere are described eg. In Reszka and Rodan, Mini-Reviews in Medicinal Chemistry, 2004, Vol 4, p. 712, FIG. 3.

Felinine (2-amino-7-hydroxy-5,5-dimethyl-4-thiaheptanoic acid) (HOOCCH(NH$_2$)CH$_2$SC(CH$_3$)2CH$_2$CH$_2$OH) is an important sulphur containing amino acid known to be present in large amounts in the urine of male cats. It has been postulated that felinine plays a role as a male pheromone designed to attract female cats (Hendriks W H, Woolhouse A D, Tartelin M F, Moughan P J (1995b) Synthesis of felinine, 2-amino-7-hydroxy-5,5-dimethyl-4-thiaheptanoic acid. Bioorg Chem 23: 89-100). So far, felinine has not been shown to be present in other species than cat.

Renal metabolites of a derivative of felinine, γ-glutamylfelinylglycine, were recently identified in the blood of domestic cats (W. H. Hendricks, D. R. Harding, K. J. Rutherfuurd-Marwick (2004), Isolation and characterization of renal metabolites of, γ-glutamylfelinylglycine in the urine of the domestic cat (*Felis catus*), Comp Biochem Physiol B Biochem Mol Biol 139, 245-251). This tripeptide is metabolised by the kidney in a similar manner to glutathione-S-conjugates in other animal species. In addition to the previously described presence of free felinine, the presence of several felinine-containing metabolites, including N-acetyl felinine, felinylglycine and unaltered γ-glutamylfelinylglycine was shown in cat urine. The renal metabolism of γ-glutamylfelinylglycine in cats generally occurs in a similar manner to glutathione S-conjugates as in other animal species, although the detection of felinylglycine indicates that subtle differences may exist.

DESCRIPTION OF THE INVENTION

The present invention relates to a novel biomarker which can be used in methods to determine the extent to which a compound interferes with steroid metabolism. Said biomarker can be any naturally occurring derivative of 2-amino-7-hydroxy-5,5-dimethyl-4-thiaheptanoic acid, which is also known as felinine. Such derivatives include compounds of the formula

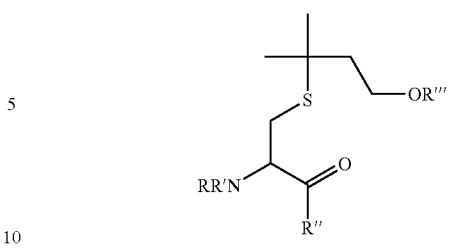

Wherein R, R', R" and R'" are independently: H, CH$_3$, COCH$_3$, COH, OCH$_3$, OC$_2$H$_5$, Gly, Gln, Glu, Ala, Val, Met, Phosphate, or Pyrophosphate.

Preferred embodiments of the marker are gamma-glutamylfelinylglycine (3-methylbutanolgluthatione), felinylglycine, felinine or N-acetyl-felinine.

The marker hereinbefore described is used in a method of determining the extent of interference of a substance with steroid metabolism comprising:

determining the presence or absence of said marker in a body fluid, and intact tissue or a tissue extract of a subject treated with said substance, wherein the presence of N-acetyl-felinine is indicative of a substance which interferes with steroid metabolism, and the absence of N-acetyl-felinine is indicative of a substance which does not interfere with steroid metabolism.

A body fluid may be any fluid derivable from a body, such as blood, plasma, serum or urine. Intact tissue is any type of issue that was removed from the body prior to analysis according to the present invention. A tissue extract is any extract from a tissue that was removed from the body, which is obtained using extraction methods well known in the art. The method herein described is an ex-vivo, in situ or in vitro method carried out on samples (body fluids, intact tissues, tissue extracts) after they were removed from the body.

In one embodiment of the present invention, the extent of interference with farnesyl diphosphate production is determined. Preferably, the body fluid is urine, plasma, or serum. In a most preferred embodiment, the presence or absence of N-acetyl-felinine is determined in urine of a subject.

The term "extent of interference with steroid metabolism" relates to the correlation between production of felinine derivatives and steroid metabolism, such as inhibition of FPP. Thus, higher levels of felinine derivatives correlate with strong interference (e.g. stronger inhibition of FPP), while low or undetectable levels of felinine derivatives correlate with a weaker interference (e.g. a more subtle inhibition of FPP, which may be caused by a different mechanism of inhibition and leads to a lower inhibition, e.g. of protein prenylation). Thus, there is a correlation between production of felinine derivatives and farnesyl diphosphate production.

The term "subject" as used herein relates to any mammal, preferably to a human subject. It is to be understood, though, that none of the methods herein described are performed directly on the body of subject. Thus, they are not in vivo methods.

It was found that N-acetyl-felinine could be used to differentiate between different bisphosphonates, ibandronate and zoledronate.

Figure 1B:
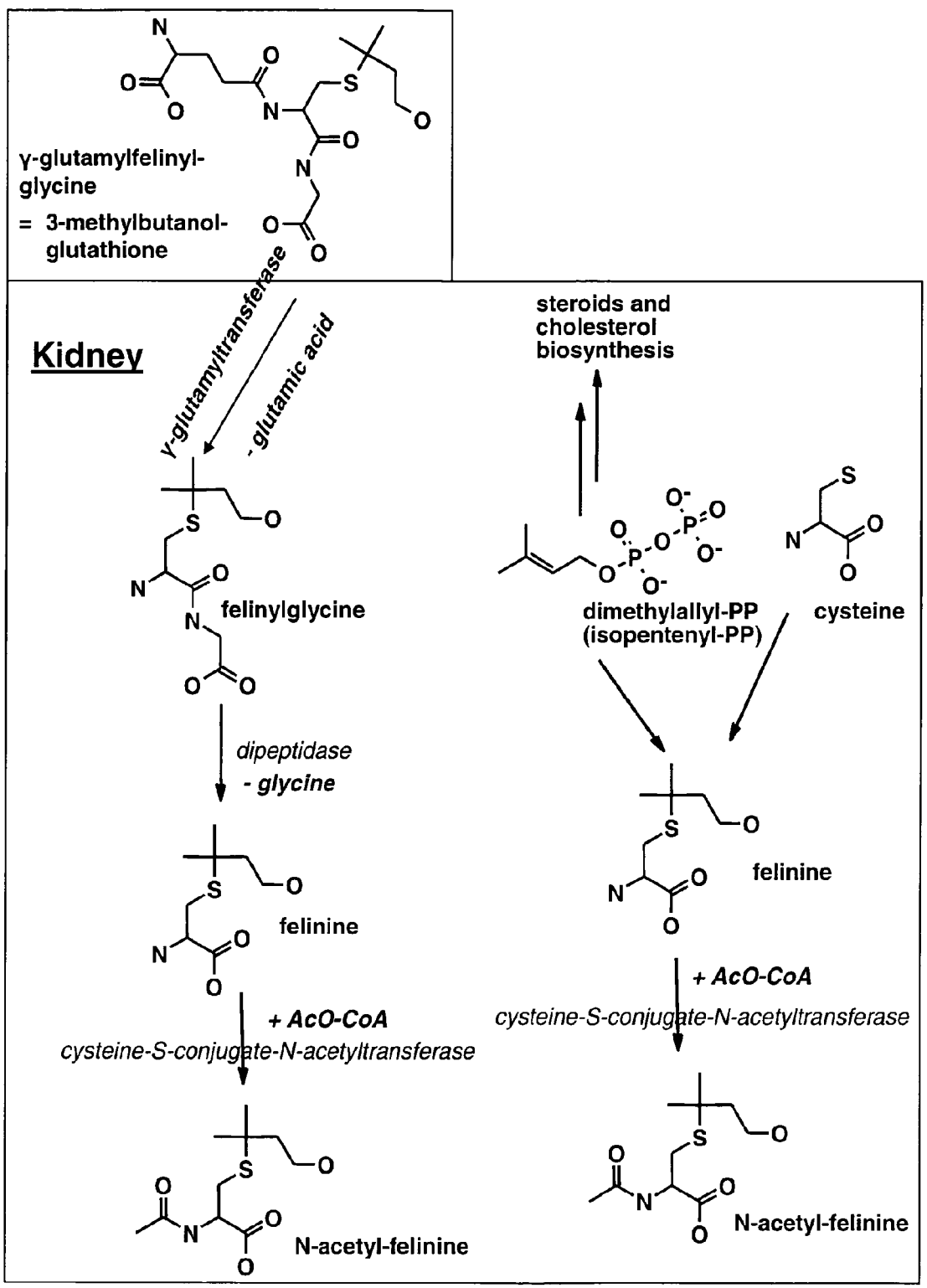

Bisphosphonates are analogs of pyrophosphate in which the geminal oxygen has been substituted by carbon (see FIG. 1 in Mini-Reviews in Medicinal Chemistry, 2004, Vol 4, p. 712)

Figure 2:
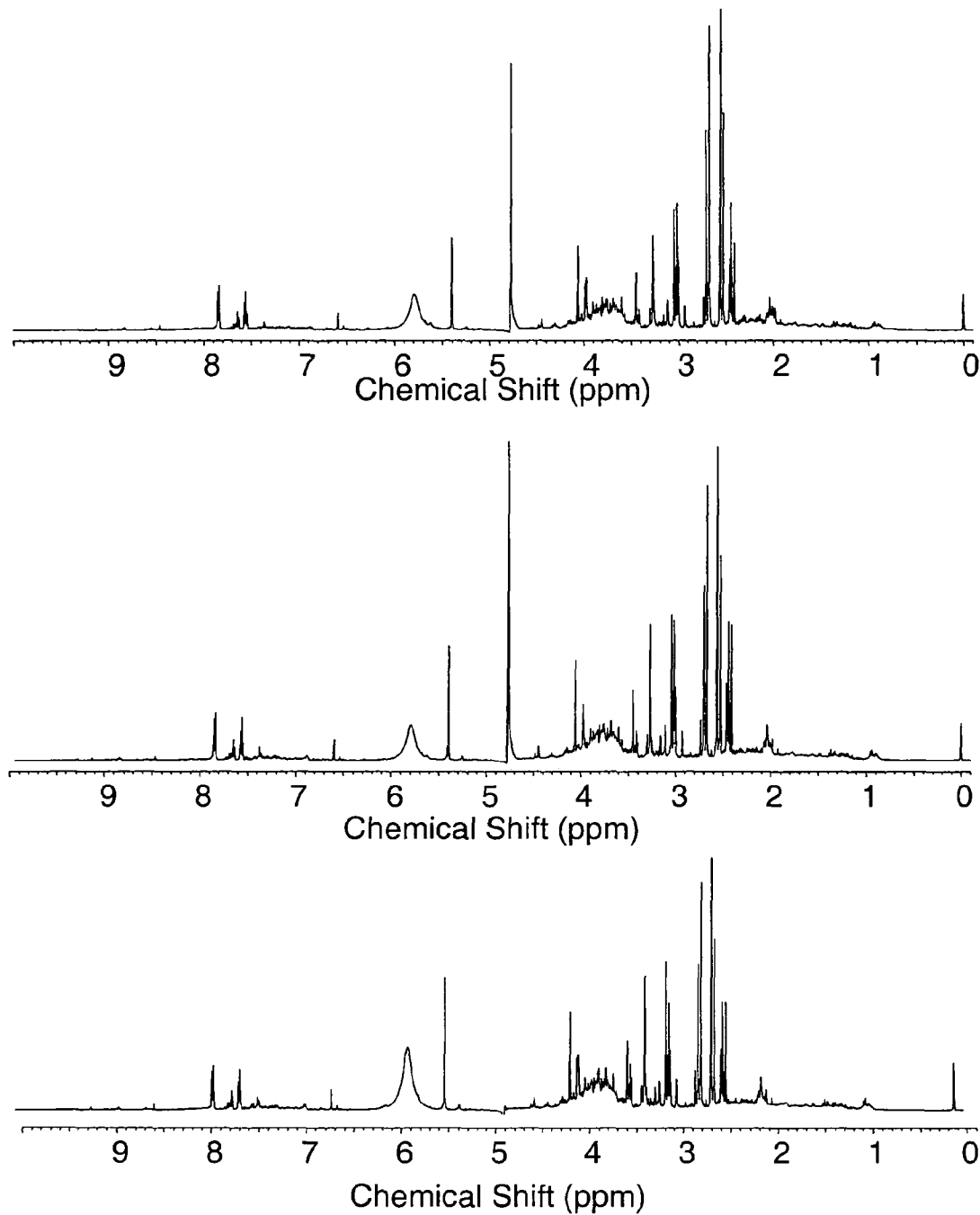

Ibandronate structure see e.g. FIG. 2 in Mini-Reviews in Medicinal Chemistry, 2004, Vol 4, p. 712

Zoledronate structure see eg. FIG. 2 in Mini-Reviews in Medicinal Chemistry, 2004, Vol 4, p. 712

Although they can both inhibit FPP synthase and, thus, interfere with sterol synthesis, they do so to a different extent. Thus, it was found that in a given time interval, zoledronate stimulation caused high levels of N-acetyl-felinine in urine, while with ibandronate stimulation, N-acetyl-felinine levels in urine were undetectable. Thus, according to the present invention, a method of differentiating between ibandronate and zoledronate in a subject treated with a ibandronate or zoledronate is also provided, said method comprising determining the presence or absence of N-acetyl-felinine or another natural derivative of felinine in a body fluid, intact tissue or tissue extract of a subject treated with said substance, wherein the absence of N-acetyl-felinine or another natural derivative of felinine is indicative of whether the patient is treated with ibandronate or zoledronate. Preferably, the body extract is urine, plasma, or serum. In a most preferred embodiment, the presence or absence of N-acetyl-felinine is determined in urine of a subject.

The identification and quantification can either be achieved by NMR or LC/GC-MS.

According to the present invention, N-acetyl-felinine or any naturally occurring derivative of felinine can also be used as a marker for bisphosphonate-induced toxicity, in particular kidney toxicity. In Zoledronate treated animals kidney and liver toxicity was observed in histopathology but not so for Ibandronate.

Furthermore, the present invention provides for the use of a felinine derivative of the formula

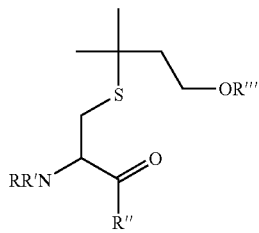

wherein R, R', R" and R'" are independently: H, $CH_3$, $COCH_3$, COH, $OCH_3$, $OC_2H_5$, Gly, Gln, Glu, Ala, Val, Met, Phosphate, or Pyrophosphate, as a marker for changes in post-translational protein prenylation of signaling proteins.

A number of metabolic pathways depend on protein prenylation. Decrease in protein prenylation, therefore, affects such metabolic pathways.

SHORT DESCRIPTION OF FIGURES

FIG. 1a, b): Pathways for the synthesis of N-acetyl-felinine in cats. Pathways for the synthesis of N-acetyl-felinine reported for cat species. Two syntheses are proposed, which both need isopentenyl (link to steroid synthesis!). One synthesis is assumed to happen in the kidney, the other synthesis is assumed to start in the liver, whereby the tripeptide is transported via blood to the kidney and metabolized to n-acetyl-felinine. The yellow box marks structures and reactions assumed in the kidney, the blue box marks reactions assumed to happen in the liver and the magenta box marks the tripeptide, which is transported from the liver to the kidney by blood. A differentiation between the liver synthesis and the pure kidney synthesis should be possible by looking for the tripeptide in plasma.

FIG. 2: NMR spectra of three rats before dosing

Figure 3A:
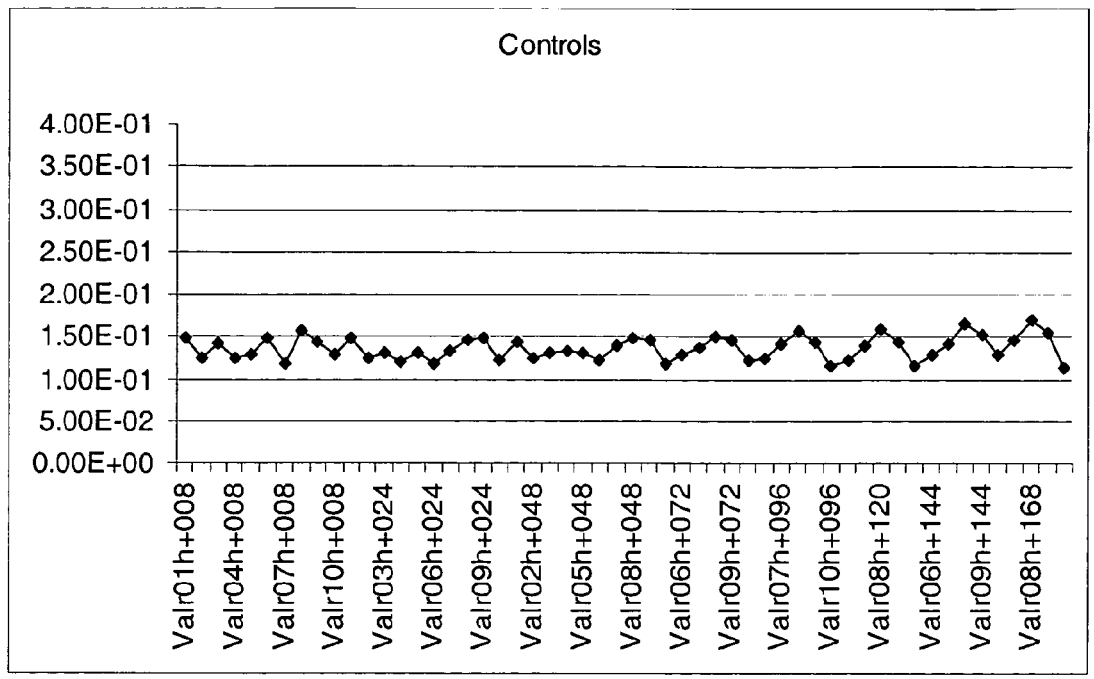
Figure 3B:
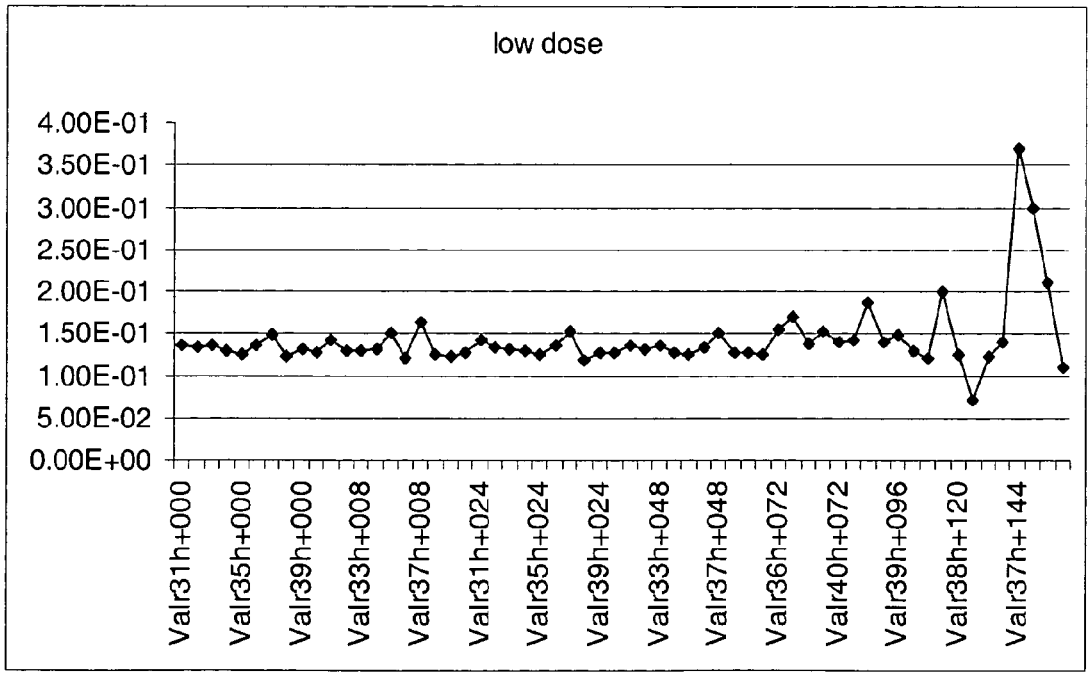
Figure 3C:
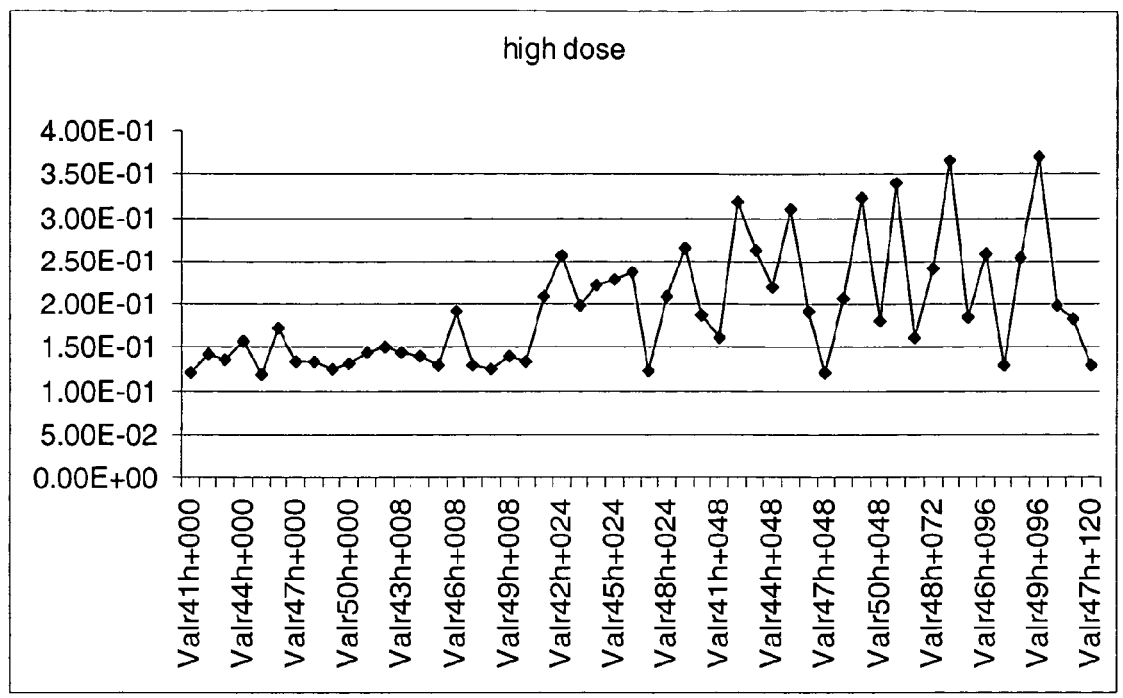

FIG. 3a)-c): Time course of bin 1.32 ppm (Methyl signals of N-Acetyl felinine) relative to creatinine: Note: Ibandronat dosed rats show no increase in bin 1.32!

Figure 4A:
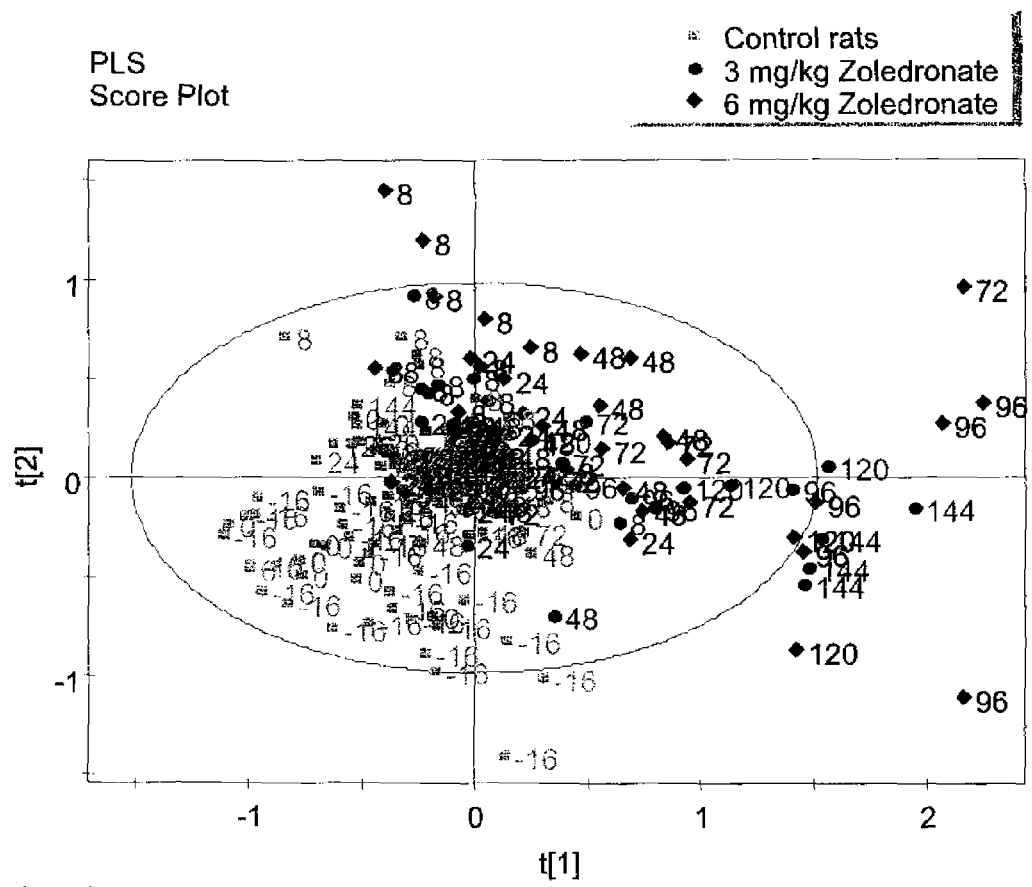
Figure 4B:
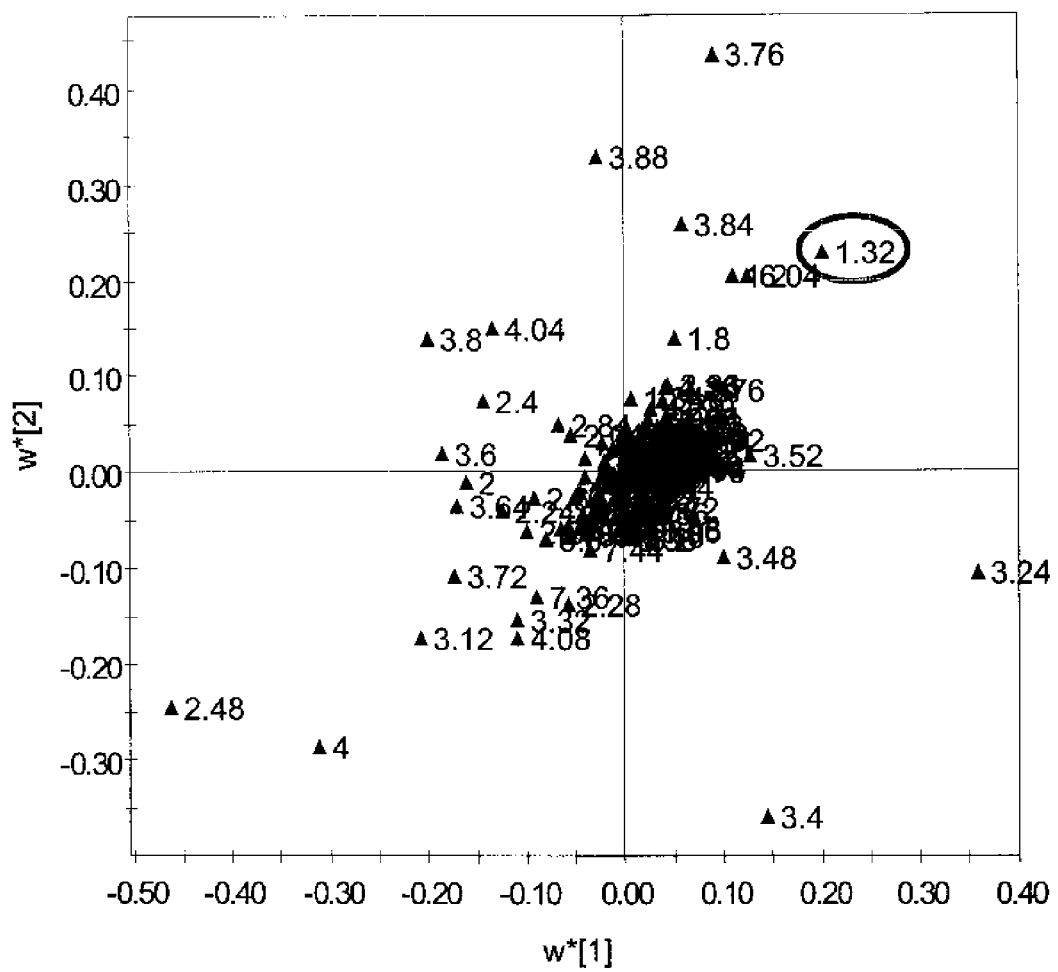
Figure 4C:
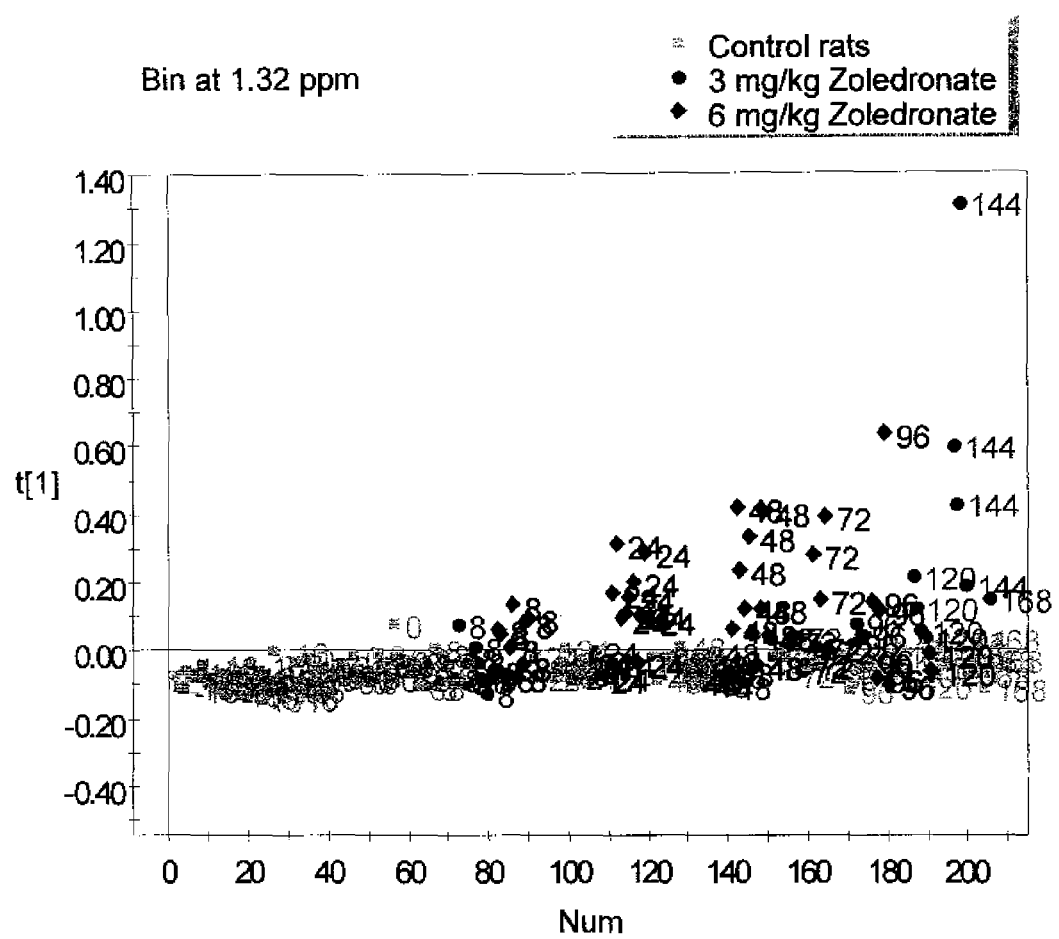

FIG. 4a)-c): Statistical analysis of rat urine NMR spectra reveals an important signal at 1.32 ppm FIG. 5: NMR spectra of three rats 96 h after dosing: New signal at 1.32 ppm visible for Zoledronate dosed rats only.

Figure 6:
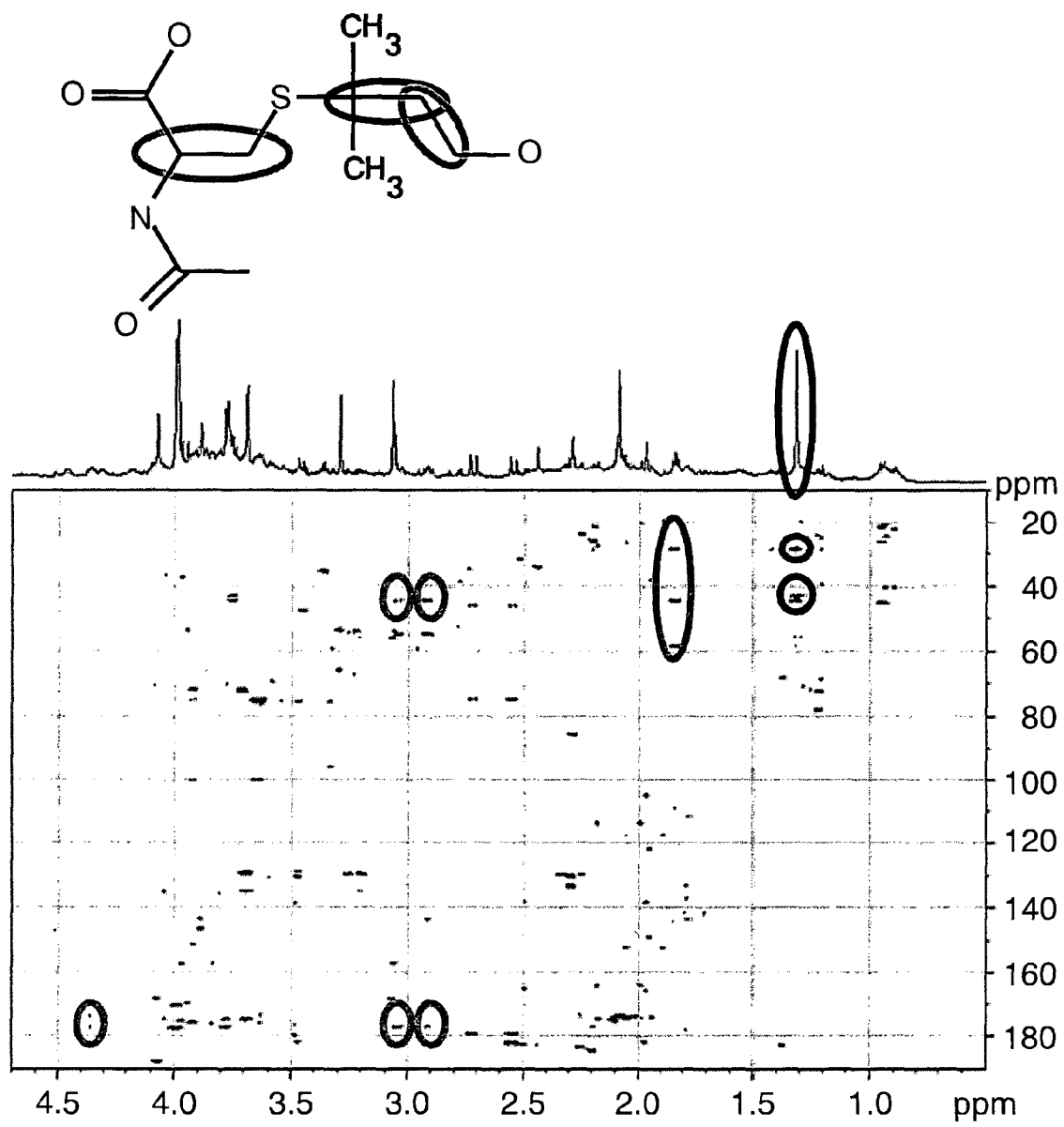
Figure 7:
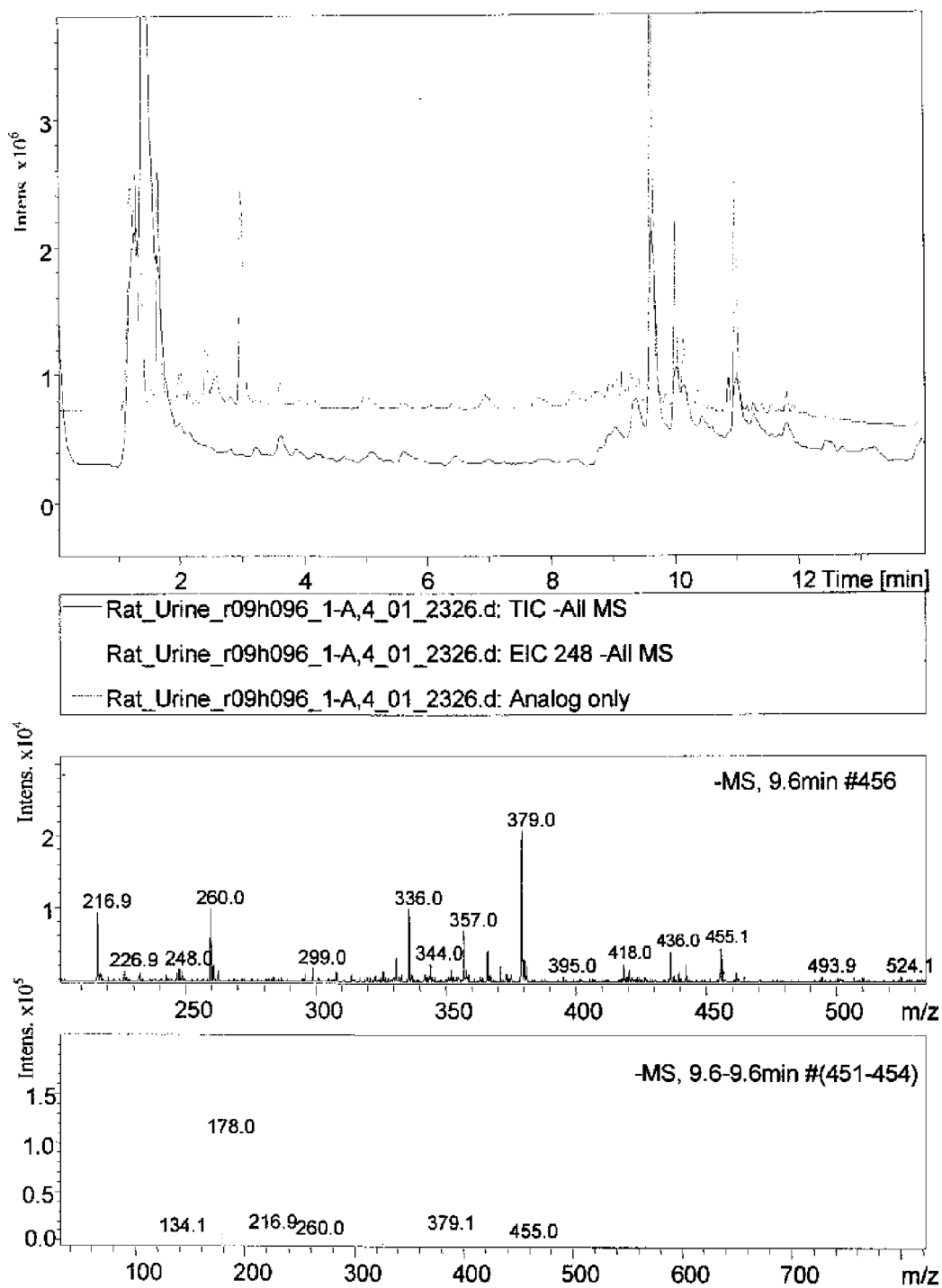

FIG. 6: 2D, 1H, 13C HMBC spectrum of urine of rats dosed with 6 mg/kg Zoledronate for structure elucidation of N-acetyl felinine FIG. 7: LC-MS investigation of rat urine: Rat control group; No signal found (green extracted ion chromatogram and in the middle MS trace for RT 9.6 min) for expected mass of N-acteyl felinine (m/z 248 in neg. mode).

Figure 8:
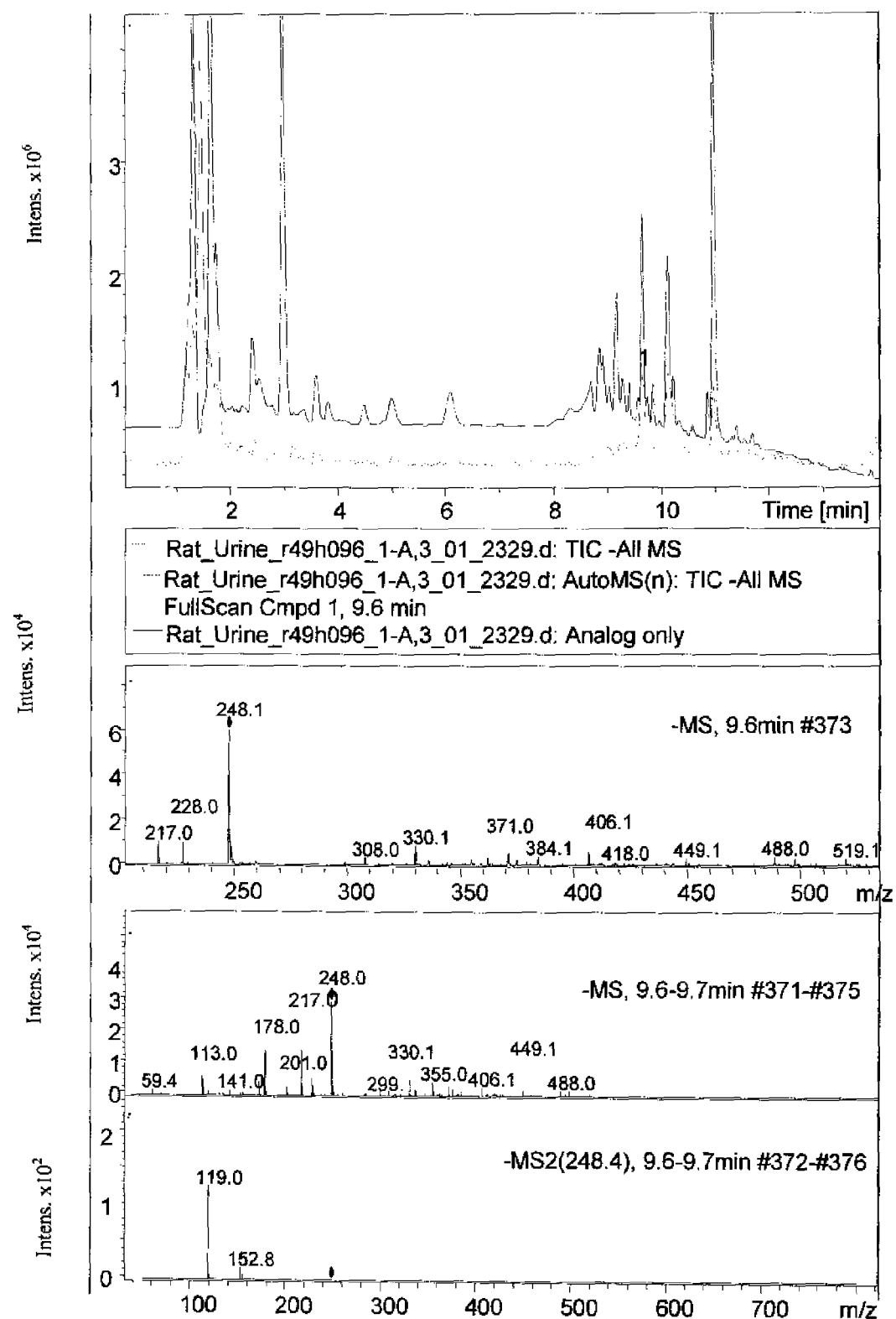

FIG. 8: LC-MS investigation of rat urine: Rat of group dosed with 6 mg/kg Zoledronate, 96 h after dosing: Strong signal found (red extracted ion chromatogram and in the middle MS trace for RT 9.6 min) for expected mass of N-acteyl felinine (m/z 248 in neg. mode). MS/MS shows expected fragmentation pattern (m/z 119)

Figure 9:
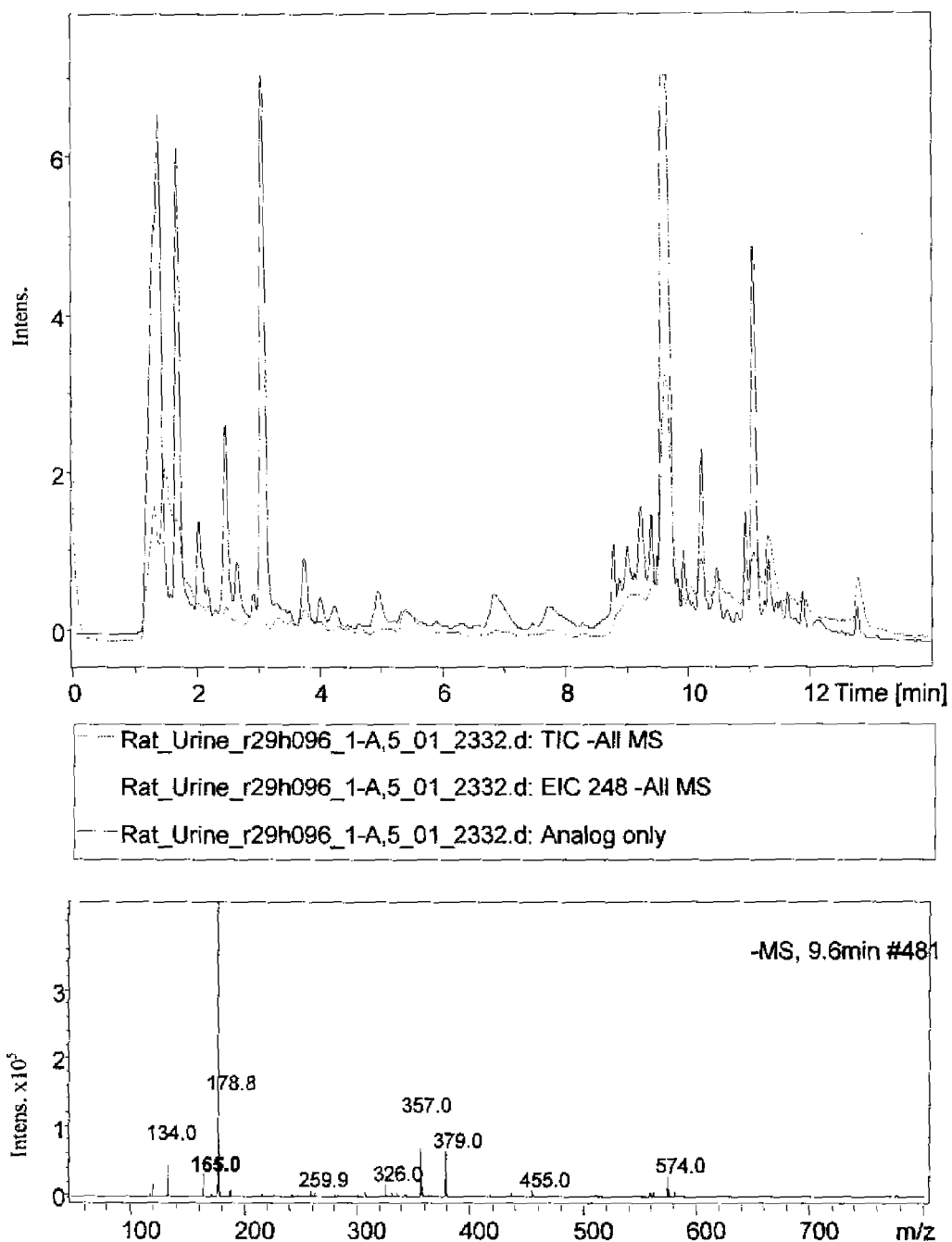

FIG. 9: LC-MS investigation of rat urine: Rat of group dosed with 3 mg/kg Ibandronate, 96 h after dosing; No signal found for expected mass of N-acteyl felinine (m/z 248 in neg. mode).

Figure 10:
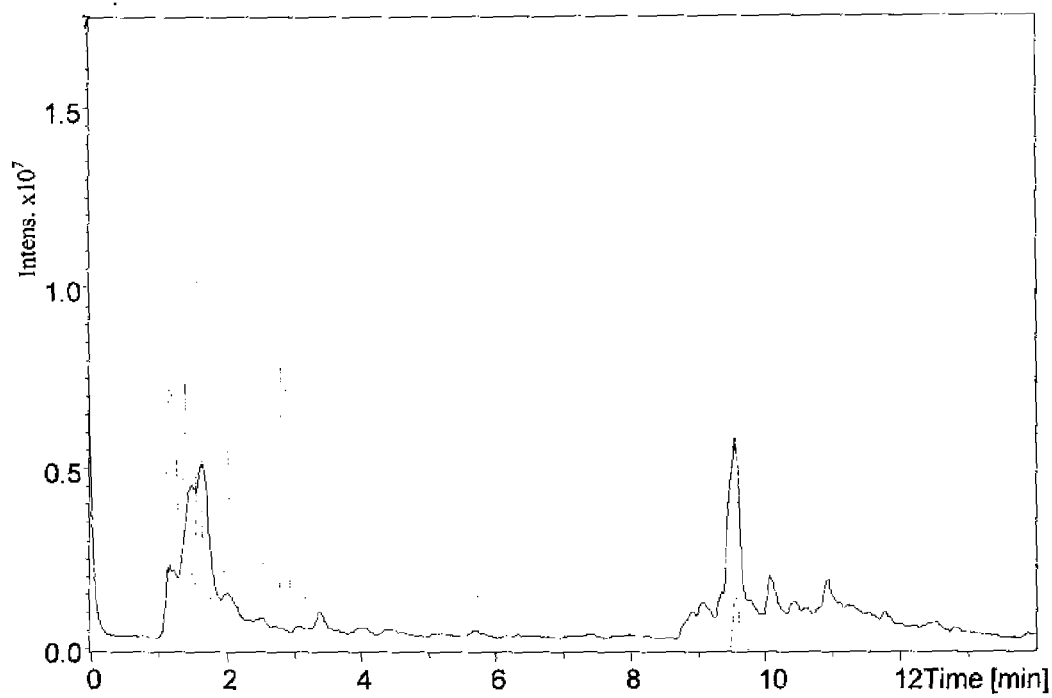
Figure 10:
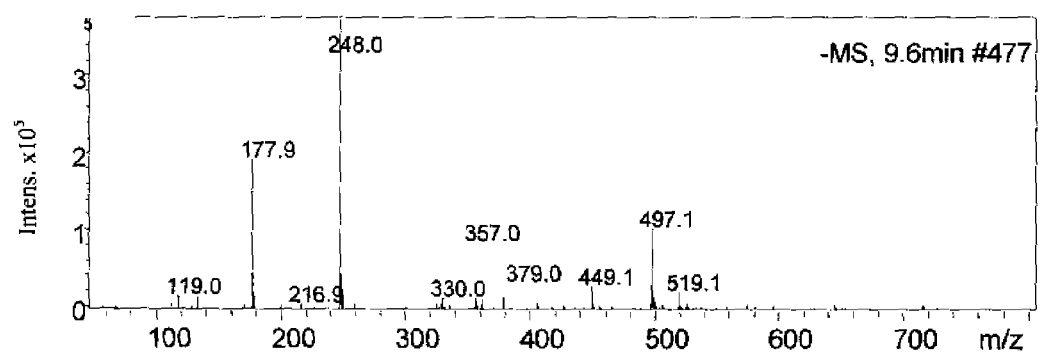

FIG. 10: LC-MS investigation of rat urine: Rat control group spiked with N-acetyl felinine; Strong signal found for expected mass of N-acteyl felinine (m/z 248 in neg. mode).

EXAMPLES 1.1 Test System

| Test system | Crl:CD ®(SD)IGS.BR (SPF) Sprague Dawley rats |
|---|---|
| Rationale | Standard strain for all COMET studies. |
| Source | Charles River Deutschland GmbH Sulzfeld/Germany |
| Group allocation | Groups 1-5: 10 males each |
| Total number of animals | 50 males |
| Age at delivery | Approximately 6 weeks (8 weeks at treatment start) |
| Identification | Cage card and ear tattoo. |
| Randomization | Computer-generated random algorithm |

1.2 Allocation

| | | | | | No. of animals (Animal numbers) | |
|---|---|---|---|---|---|---|
| Allocation | Compound | Dose mg/kg] | Dose Volume [ml/kg] | No. of doses | Subgroup A Necropsy 48 hours after application | Subgroup B Necropsy 168 hrs after application |
| 1* | Vehicle | 0 | 2 | 1 | 5 (1-5) | 5 (6-10) |
| 2 | Compound 1 | 1 | 2 | 1 | 5 (11-15) | 5 (16-20) |

-continued

| Allocation | Compound | Dose mg/kg] | Dose Volume [ml/kg] | No. of doses | No. of animals (Animal numbers) | |
|---|---|---|---|---|---|---|
| | | | | | Subgroup A Necropsy 48 hours after application | Subgroup B Necropsy 168 hrs after application |
| 3 | Compound 1 | 3 | 2 | 1 | 5 (21-25) | 5 (26-30) |
| 4 | Compound 2 | 3 | 2 | 1 | 5 (31-35) | 5 (36-40) |
| 5 | Compound 2 | 6 | 2 | 1 | 5 (41-45) | 5 (46-50) |

*Control animals were treated with vehicle, only.

1.3 Husbandry

Conditions Standard Laboratory Conditions. Air-conditioned with 10-15 air changes per hour, and continuously monitored environment with target ranges for temperature 22±3° C. and for relative humidity between 30-70%. 12 hours fluorescent light/12 hours dark cycle, with music during the light period.

Accommodation Individually in Makrolon type—3 cages with wire mesh tops and standardized softwood bedding ('Lignocel' Schill AG, CH-4132 Muttenz/Switzerland) during most days of the acclimatization period as well as individually in metabolism cages (>300 g, Tecniplast, Italy) on three days (day-7, day-4 and day-1) of the acclimatization period and the entire sampling period.

Diet Purina chow 5002 certified rodent diet non-pelleted (PMI® Nutition International, LLC P.O. Box 19798, Brentwood, Mo. 63144 U.S.A.) ad libitum. Provided to animals from the beginning of the acclimatization period.

Water Community tap-water, from Itingen ad libitum. Results of representative bacteriological, chemical and contaminant analyses are presented in Appendix I. See pp. 110-113

1.4 Test Items
Compound 1: Ibandronate in saline solution
Compound 2: Zoledronate in saline solution
Control/Vehicle: Saline Solution (0.9%)

1.5 Urine Sampling

Urine samples were collected in metabolism cages at 0 to 4° C. (automatically refrigerated by a Tecniplast sampling/cooling unit) at the intervals given in the sampling schedule below into sample tubes containing 1 ml of an aqueous Cs-azide (1%) solution. Before aliquoting, urine volumes were determined.

Immediately after reaching the end of the sampling period, the volume was determined and the samples were centrifuged at 3000 u/min [500 g] for 10 min.

1.6 Determination of N-Acetyl-Felinine by NMR and LC-MS

N-acetyl-felinine was identified in urine samples on basis of 1D and 2D NMR spectra. Spectra were acquired at 600.13 MHz on a Bruker AV 600 spectrometer and at 500.13 MHz on Bruker DRX-500 spectrometer. Urine samples were prepared and measured and the data evaluated as described elsewhere (Keun, H. C.; Ebbels, T. M. D.; Antti, H.; Bollard, M. E.; Beckonert, O.; Schlotterbeck, G.; Senn, H.; Niederhauser, U.; Holmes, E.; Lindon, J. C.; Nicholson, J. K. *Chem. Res. Toxicol.* 2002, 15, 1380-1386).

Aliquots of 400 microliter urine are transferred into well plates. For adjustment of urinary pH 200 microliter of buffer [ca. 0.2M Na2HPO4/NaH2PO4, ca. 1 mM TSP (3-trimethylsilyl-D4-propionic acid), ca. 3 mM sodium azide] is added to each well. Prepared well plates are centrifuged at ca. 3,000 rpm at 4° C. for 5-10 min to remove insoluble material.

$^1$H NMR spectra for Metabonomic analysis (e.g. at 500 Mhz, 64 k data points, 12019.2 Hz spectral width) were measured at 300K. The water resonance were suppressed by use of standard pulse-sequences (e.g noesyprld, irradiation for 2 s relaxation delay and during 100 ms mixing time). For each sample as many transients were added as is needed to provide spectra high enough in signal to noise. Fourier transformation was done by use of a matched window function (e.g. lb=1) followed by (automatic or manual) phasing and base-line correction. Referencing was done with respect to TSP added (defined as 0.0 ppm). Acquisition and processing of spectra was performed with Bruker XWinNMR 3.5 software.

| Study Day | | | Sample time points relative to the application time point and sample labels for samples sent to Roche | | | |
|---|---|---|---|---|---|---|
| Absolute day of urine sample | Dates of urine sample | | | Groups 1-5 | | |
| Days | collection | collection | Time | Subgr. A | Subgr. B | Label |
| -12 | -12 to -11 (24 h) | 14.-15.04.04 | Arriv. to -264 h | X | X | -264 h |
| -4 | -4 to -3 (0-24 h) | 22.-23.04.04 | -96 h to -72 h | X | X | -72 h |
| -1 | -1 (pre-dose) | 25.04.04 | -24 h to -16 h | X | X | -16 h |
| -1 | -1 to 1 (pre-dose)* | 25.-26.04.04 | -16 h to 0 h | X | X | 0 h |
| 1 | 1 (1$^{st}$ dose) | 26.04.04 | 0 h to 8 h | X | X | 8 h |
| 1 | 1 to 2 | 26.-27.04.04 | 8 h to 24 h | X | X | 24 h |
| 2 | 2 to 3* | 27.-28.04.04 | 24 h to 48 h | X | X | 48 h |
| 3 | 3 to 4 | 28.-29.04.04 | 48 h to 72 h | | X | 72 h |
| 4 | 4 to 5 | 29.-30.04.04 | 72 h to 96 h | | X | 96 h |
| 5 | 5 to 6 | 30.-01.05.04 | 96 h to 120 h | | X | 120 h |
| 6 | 6 to 7 | 01.-02.05.04 | 120 h to 144 h | | X | 144 h |
| 7 | 7 to 8* | 02.-03.05.04 | 144 h to 168 h | | X | 168 h |

*this samples were undergo additional special urine analysis as described below.

Each spectrum recorded was reduced in size for simplified statistical analysis (e.g. For NMR spectra recorded according to the standard protocol 245 variables will be calculated by equidistant integration between 0.2-10.0 ppm). Regions containing misleading information (e.g. solvents, urea cover a region for 4.5 up to 6.0 ppm) were excluded or merged (e.g. the region from 2.66 to 2.74 ppm serves as a value indicative for citrate) prior to analysis. To take account variations in urine concentration, all data-reduced spectra were normalised to a constant integrated intensity of 100 units.

The multivariate data analysis identifies signals, patterns of signals, and metabolites derived thereof, which are significantly different between individuals and groups of individuals. Thereby widespread PCA (principal component analysis) is used for identifying significant patterns of signals and assigning these patterns to samples and groups of samples. PLS (projection to latent structures, partial least squares) is also used for finding significant patterns of signals, whereby in contrast to PCA the information of dose-groups is used for boosting the identification of significant changes. The assignment is performed with the help of an internal data base of metabolites, with the help of pathway mapping procedures (KEGG database) and with the help of a spectroscopic structure elucidation for unknown metabolites when feasible.

Figure 5:
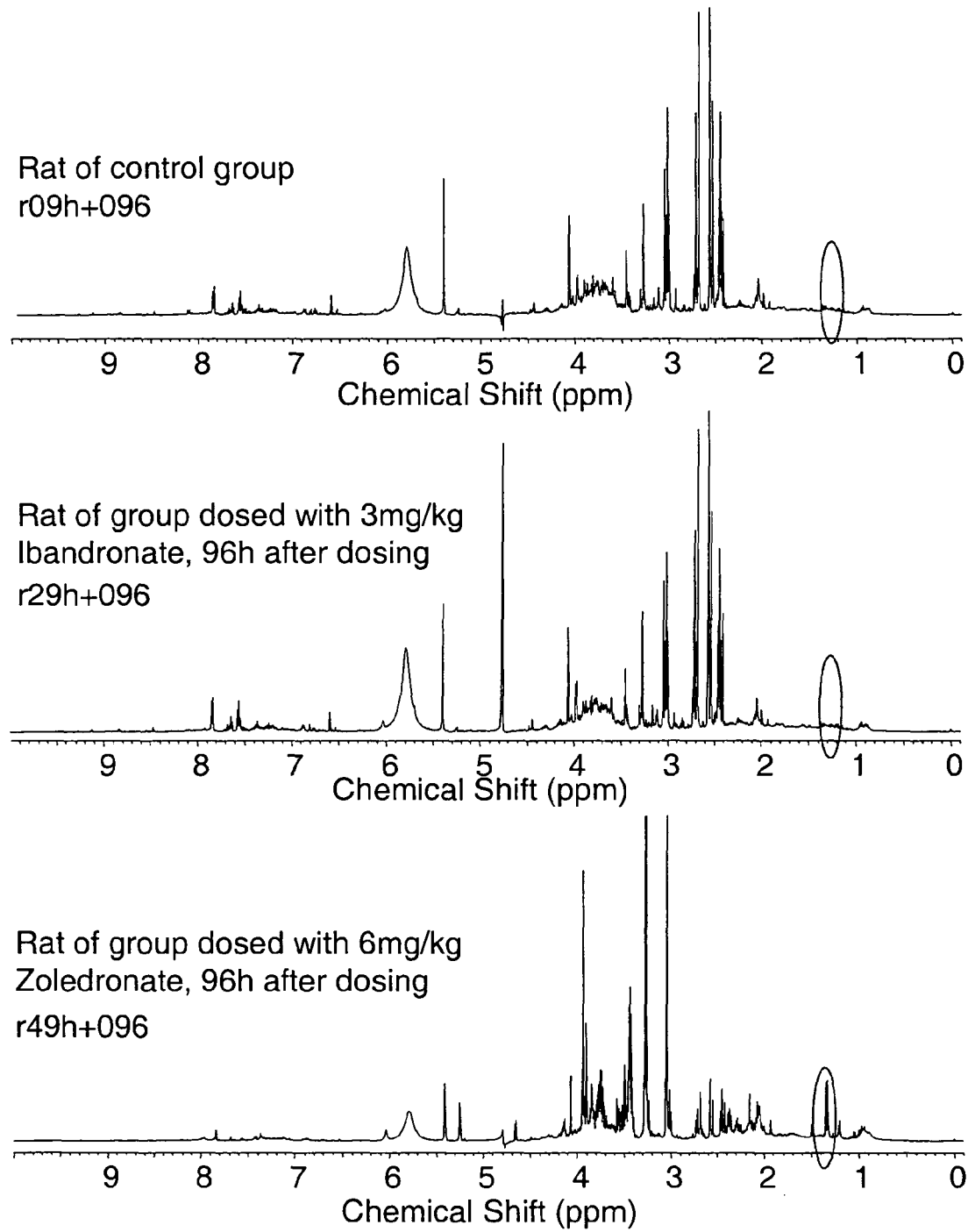

N-acetyl-felinine was found in spectra of rats dosed with Zoledronate (see FIG. 5). A signal at 1.32 ppm was observed in the 1D NMR spectra and the structure was elucidated on basis of 2D NMR experiments (see FIG. 6).

LC-MS

In addition N-acetyl-felinine was also determined in LC-MS experiments of urine samples.

LC-MS analysis of urine was performed using an Agilent 1100 HPLC system coupled to a Bruker Esquire 3000+ mass spectrometer equipped with an electrospray interface. Urine samples were diluted 4-fold with distilled water and 2 μl injections were made from a well plate maintained at 4° C. into a 150 mm×3.9 mm Waters Atlantis dC18 3 μm HPLC column maintained in an oven at 30° C. The column was eluted at a flow rate of 1 ml/min; mobile phase A consisted of 20 mM ammonium acetate, and mobile phase B of acetonitrile. A gradient elution started with 100% A for 5 min was linearly increased to 95% B in 15 min and maintained at 95% B for 3 min, returned to 100% A over 1 min, and then reequilibrated over a final 5 min prior to injection of the next sample. The mass spectrometer was operated in negative mode with a dry gas flow of 8 l/min, nebulizer pressure of 27 psi and dry temperature of 330° C. The instrument was set to acquire over the mass range m/z 50-800. N-acetyl-felinine was found under this conditions at a retention time of 9.6 min with the expected m/z 248 (see FIG. 8) in samples of rats dosed with Zoledronate. MS/MS experiments revealed the expected fragment m/z 119.

In LC-MS N-acetyl-felinine can also be measured in positive mode. Here the corresponding mass of the M+H$^+$ is found at m/z 250.

The invention claimed is:

1. A method of determining the extent of interference of a bisphosphonate with steroid metabolism comprising:

determining the presence or absence of a felinine derivative selected from the group consisting of gamma-glutamylfelinylglycine (3-methylbutanolgluthatione), felinylglycine, felinine or N-acetyl-felinine in a body fluid, and intact tissue or a tissue extract of a subject treated with said bisphosphonate, wherein the presence of said felinine derivative is indicative of a bisphosphonate which interferes with steroid metabolism, and the absence of said felinine derivative is indicative of a bisphosphonate which does not interfere with steroid metabolism wherein the extent of interference with farnesyl diphosphate production is determined, and wherein further the subject is a rat, and wherein further the bisphosphonate is selected from the group consisting of ibandronate and zoledronate.

2. The method of claim 1, wherein said interference is determined in a body fluid which is urine, plasma or serum.

3. A method of differentiating between ibandronate and zoledronate in a subject treated with aminobisphosphonate compound, comprising determining the presence or absence of a felinine derivative of the formula

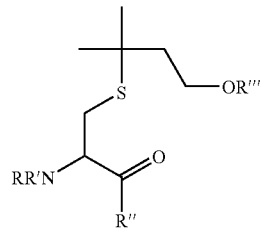

wherein R, R', R'' and R''' are independently.: H:, CH$_3$, COCH$_3$, COH, OCH$_3$, OCH$_2$H$_5$, Gly, Gln, Glu, Ala, Val, Met, Phosphate, or Pyrophosphate in a body fluid, intact tissue or tissue extract of a subject treated with said substance, wherein the presence of said felinine derivative is indicative of the subject treated with zoledronate, and wherein the absence of said felinine derivative is indicative of the subject treated with ibandronate.

4. The method of claim 3, wherein said body fluid is urine, plasma or serum.

5. A method of differentiating between ibandronate and zoledronate in a subject treated with aminobisphosphonate compound, comprising determining the presence or absence of a felinine derivative, wherein said felinine derivative is gamma-glutamylfelinylglycine (3-methylbutanolgluthatione), felinylglycine, felinine or N-acetyl-felinine, in a body fluid, intact tissue or tissue extract of a subject treated with said substance, wherein the presence of said felinine derivative is indicative of the subject treated with zoledronate, and wherein the absence of said felinine derivative is indicative of the subject treated with ibandronate.

* * * * *